United States Patent
Holland

(10) Patent No.: US 7,041,869 B2
(45) Date of Patent: May 9, 2006

(54) TRANSGENIC LUCIFERASE MOUSE

(75) Inventor: Eric Charles Holland, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/679,231

(22) Filed: Oct. 3, 2003

(65) Prior Publication Data

US 2004/0139487 A1    Jul. 15, 2004

Related U.S. Application Data

(60) Provisional application No. 60/416,001, filed on Oct. 4, 2002, now abandoned.

(51) Int. Cl.
*A01K 67/00* (2006.01)
(52) U.S. Cl. .................................. 800/8; 800/3; 800/21
(58) Field of Classification Search .................... 800/8, 800/9, 10, 13, 14, 18, 3, 21
See application file for complete search history.

(56) References Cited

OTHER PUBLICATIONS

Vooijs et al. "Noninvasive imaging of spontaneous retinoblastoma pathway-dependent tumors in mice." Cancer Research 62:1862-1867, 2002.*
Kappel et al. "Regulating gene expression in transgenic animals." Current Opinion in Biotechnology 3:548-553, 1992.*
Sandal T "Molecular aspects of the mammalian cell cycle and cancer." The Oncologist 7:73-81, 2002.*
Mullins et al. "Transgenesis in nonmurine species." Hypertension 22:630-633, 1993.*
Houdebine LM "Production of pharmaceutical proteins from transgenic animals." Journal of Biotechnology 34: 269-287, 1994.*
Wall RJ "Transgenic livestock progress and prospects for the future" Theriogenology 45:57-68, 1996.*
Cameron ER "Recent advances in transgenic technology" Molecular Biotechnology 7:253-265, 1997.*
Sigmund CD "Viewpoint: Are studies in genetically altered mice out of control?" Arterioscler Thromb Vasc Biol 20:1425-1429, 2000.*
Niemann H "Transgenic farm animals get off the ground." Transgenic Research 7:73-75, 1998.*
Bhaumik et al. "Optical imaging of *Renilla luciferase* reporter gene expression in living mice." PNAS 99(1): 377-382.*
Hasan et al. "Long-term, noninvasive imaging of regulated gene expression in liviing mice." Genesis 29:116-122, 2001.*
Steghens et al. (1998) *Firefly luciferase* has two nucleotide binding sites:effect of nucleoside monophosphate and CoA on the light-emission spectra. Biochem J. 336:109-113.*
Markova et al. (2004) Cloning and Expression of cDNA for a luciferase from Marine Copepod Metridia Ionga. J. Biol. Chem. 279:3212-3217.*
Müller, C. et al. Methylation of the Cyclin A1 Promoter Correlates with Gene Silencing in Somatic Cell Lines, While Tissue-Specific Expression of Cyclin A1 Is Methylation Independent: *Molecular and Cellular Biology*, May 2000, vol. 20, No. 9, pp. 3316-3329.
Dieckmann, A. et al. The EIA Transcriptional Control Region is Efficiently Activated in Proliferating Tissues of Transgenic Mice: *Oncogene*, 1994, pp. 2227-2233.
Jiang, Z. et al. Retinoblastoma Gene Promoter Directs Transgene Expression Exclusively to the Nervous System: *The Journal of Biological Chemistry*, Jan. 5, 2001, vol. 276, No. 1, pp. 593-600.
Holmberg, C. et al. E2F-1-Induced p. 53-Independent Apoptosis in Transgenic Mice: *Oncogene*, 1998, vol. 17, pp. 143-155.
Pierce, A. et al. Increased E2F1 Activity Induces Skin Tumors in Mice Heterozygous and Nullizygous for p. 53: *Proc. Natl. Acad. Sci.*, Jul. 1998, vol. 95, pp. 8858-8863.

* cited by examiner

*Primary Examiner*—Deborah Crouch
*Assistant Examiner*—Louis D. Lieto
(74) *Attorney, Agent, or Firm*—Benjamin Aaron Adler

(57) ABSTRACT

The present invention provides a transgenic animal expressing the reporter gene, luciferase, driven by a promoter (e.g. the E2F1 promoter) that acts as a sensor of cell cycle. The luciferase substrate, luciferin, emits light when metabolized, and the light is transmitted through mammalian tissues. Therefore, the transgenic animal model of the present invention allows for monitoring of areas of major cell cycle activity, a characteristic of cancer cells, under adequate visualization conditions. These transgenic animals are useful as in vivo models for testing preventative measures for cancer as well as for testing novel therapeutic modalities.

2 Claims, 8 Drawing Sheets

GAATTCCATCCGGACAAAGCCTGCGCCCCCGCCCATTGGCC
GTACCGCCCCGCCCATCCCGCGCCCTCGCCGCCGGGTCCG
GCGCGTAAAGCCAATAGAACCGCCGTTGTTCCCGTCACGCC
GGGGCAGCCAATTGTGGCGGCGCTCGCGCTCGTGGCTCTTTCGCG
GCAAAAGGATTTGGCGCGTAAAAGTGGCCGGACTTTGCAGGCAGC
GGCGGCCGGGCCGGAGCGGGATCGAGCCCTCGCCGAGGCCTGAAT
(SEQ ID NO:1)

highlighted bases are primer sequences

Log scale

Percent decreas

TRANSGENIC LUCIFERASE MOUSE

CROSS-REFERENCE TO RELATED APPLICATION

This non-provisional patent application claims benefit of priority of provisional patent application No. 60/416,001 filed Oct. 4, 2002, now abandoned.

BACKGROUND OF THE INVENTION

1. Field of the Invention

The present invention relates to the use of a transgenic animal for in vivo monitoring of animal models of human cancers. The transgenic animal is useful for testing potential preventative measures and therapeutic modalities as well as determining causative agents of cancer.

2. Description of the Related Art

The study of the molecular mechanisms of tumorigenesis has been greatly facilitated in recent years by the use of animals able to overexpress or not, at the tissue specific or general level, a variety of genes (germ line modification). However, animal models traditionally have been cumbersome because of the difficulty in quantitating tumor burden and the requirement for either bulk tumor growth or animal survival as end points to evaluate the effect of a potential therapy. Small tumors or tumors in difficult to reach areas can go undiagnosed by palpation and can be refractory to caliper measurements.

Over the years, new imaging methods have been developed to overcome this difficulty. Miniaturized imaging equipment and reporter probes have been developed improving the ability to study animal models of disease. These technologies can be used to continuously monitor in vivo tumour development, the effects of therapeutics on individual populations of cells, or even specific molecules. A variety of non-invasive high-resolution imaging methods are now available for the detection and monitoring of deep-seated cancers, as well as their metastases, in animal models. Among these are positron emission tomography (PET), magnetic resonance imaging (MRI) and computed tomography (CT).

PET is a diagnostic tool for the evaluation of cancer that takes advantage of metabolic imaging. Currently, most of these studies are performed with the glucose analog $^{18}$F-FDG, which has been shown to accumulate in high amounts in most tumors. $^{18}$F-FDG PET is used in the diagnosis, staging, and posttherapy evaluation of cancer. However PET is regarded as an expensive test, demanding technique that is time consuming and substantial expertise and training with a considerable infrastructure (cyclotron, supporting radiochemistry laboratory space, usually two PET scanners, and a significant number of support staff). Owing to the short-lived nature of positron-labeled radiopharmaceuticals, the distribution of labeled ligands off site from a hospital-based cyclotron is still restricted to $^{18}$F-labelled compounds. $^{18}$F has a half-life of 110 min, which is just long enough to allow for shipment of $^{18}$F-labelled products. These reasons make this method too cumbersome and expensive for analysis of large numbers of animals in an experimental therapy evaluation.

MRI and CT are primarily used to display an animal's internal anatomy. Structural MRI technology was developed from nuclear magnetic resonance. MRI is a noninvasive imaging technique that does not use x-rays (unlike CAT scan). The process involves passing a strong magnetic field through the body. The MRI scanner can detect radiation from certain molecules, which are present in different concentrations in different tissues. The fluid contrast between body structures can then be visualized. A cross-sectional imaging is produced in which there is significant contrast between tissues of interest. MRI is used as an imaging technique because of the very detailed pictures of anatomy that can be achieved. However, even though MRI does not need radioactive isotopes, it does require expensive equipment and time consuming analysis of the data, making it less than adequate for high throughput analysis of animal models.

More recently bioluminescence imaging based on in vivo expression of luciferase, the light-emitting enzyme of the firefly, has been used for non-invasive detection of transplanted tumors and of very specific cancer types. Transplanted tumors are, however, only a partial model of human tumorigenesis because the histology of these tumors does not resemble that of the human disease. Moreover, because these tumor models have not been predictive in preclinical trials, the biology of these tumors may not recapitulate the human disease. Specific bioluminescence tumor models are by its own nature of limited use as a tool for the general study of many different types of cancer in animal models.

Thus, there is a need in the art for a technology that could monitor, as a function of time, different aspects of a whole array of neoplasias (e.g. tumor susceptibility and development, response to drugs or external causative events, etc) in a simple, fast, economical and specific way. The present invention fulfills this long-standing need and desire in the art.

SUMMARY OF THE INVENTION

It is an object of the present invention to overcome the difficulties in the prior art of monitoring cancer progression in animal models without the need to sacrifice the animal. To this end, the present invention provides a transgenic animal expressing the reporter gene, luciferase, driven by a promoter (e.g., the E2F1 promoter) that acts as a sensor of cell cycle. The luciferase substrate, luciferin, emits light when metabolized. Light is transmitted through mammalian tissues. Therefore, the present invention allows for reporting of areas of major cell cycle activity, a characteristic of cancer cells, under adequate visualization conditions. Such a transgenic animal is named Elux.

The following experiments used the PDGF-driven oligodendrogliomas and the PDGF receptor inhibitor as proof of principle for the utility of the Elux mouse. As this is a transgenic model, it can serve as a readout for any transgenic or knockout mouse that develops tumors anywhere. The ability of Elux to sense cell cycle can be transferred to any other animal by cross-breeding. Crossing Elux with a variety of animal models having intrinsic ability to develop cancer (e.g. transgenics, knock-outs, avian leukosis virus susceptible) would enable easy monitoring of their tumors. Alternatively, Elux cancer models can be generated by the use of carcinogenic compounds. Thus, Elux is an invaluable tool to monitor cancer development, allowing sensitive, quantitative, real-time spatio-temporal analyses of uncontrolled cell growth in intact multicellular organisms. This facilitates the study of potential antineoplastic therapies and the rapid optimization of effective treatment regimens.

DESCRIPTION OF THE DRAWINGS

FIG. 2A shows a schematic diagram of the Elux transgene. FIG. 2B shows sequence analysis of the E2F1 promoter within the Elux promoter in comparison with the published E2F1 promoter sequence.

FIG. 3A: all mice were injected with luciferin prior to imaging with the Xenogen system. The activity in the limbs, nose and tail were due to heat radiating from the portions of the mouse not covered in fur. The brain tumors were generated by post-natal gene transfer of PDGF to CNS progenitors using the RCAS/tv-a system by virtue of the Ntv-a transgene. The histology of these tumors was that of high-grade oligodendrogliomas. The first mouse had a brain tumor and was transgenic for Elux. The signal from the brain tumor can be easily seen. The second mouse had a large brain tumor but is Elux$^{-/-}$. The slight signal was likely due to increased heat from the tumor due to elevated metabolism. The third and fourth mice were Elux$^{+/+}$ but did not have brain tumors. These data demonstrate that the presence of tumors can be detected in vivo with this system and that the activity of the Rb pathway in the tumors can be measured non-invasively allowing each mouse to act as its own control for studies on anti-neoplastic treatments. FIG. 3B: Histologic analysis of the glioma harbored within the mouse demonstrating intracranial luciferase activity relative to normal brain.

DETAILED DESCRIPTION OF THE INVENTION

Figure 1:
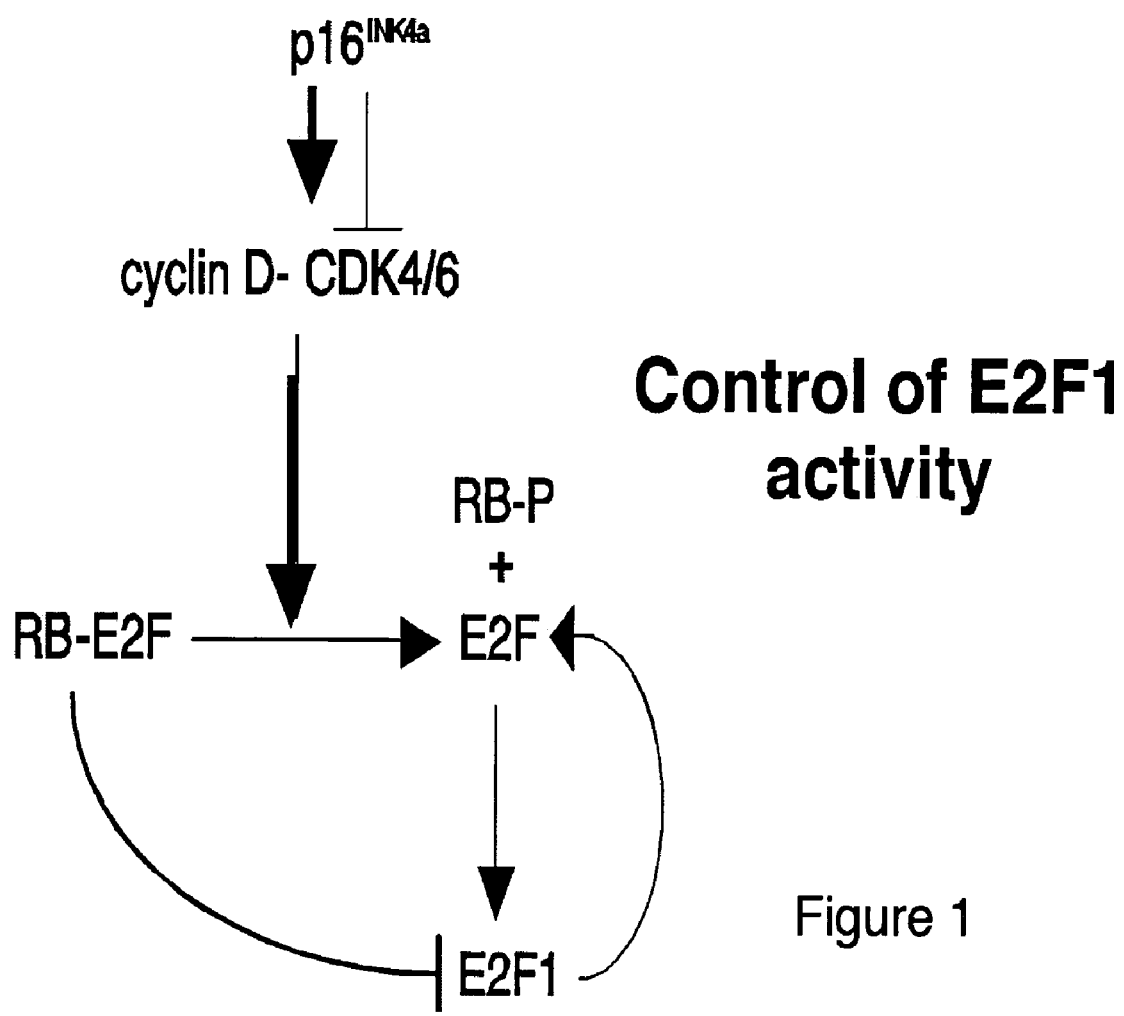
FIG. 1 shows the set of cellular signals that contribute to the activation or repression of E2F1 and the structure of the luciferase reporter construct used to create the Elux transgenic mice. The E2F-1 promoter is under E2F-dependent negative control during cell growth response, being transcriptionally repressed through E2F sites in G0 and early G1. The presence of an E2F DNA-binding complex containing the Rb-related p130 protein (Rb2) correlates with E2F-1 gene repression and that overexpression of p130 inhibits transcription from the E2F-1 promoter. D-type cyclin-dependent kinase activity specifically activates the E2F-1 promoter by relieving E2F-mediated repression but is inhibited by coexpression of the cdk4 and cdk6 inhibitor p16 (CDKN2, MTS1, INK4). These makes E2F-1 gene expression to be controlled during cell cycle progression by a regulatory network involving at least one oncogene (cyclin D1) and several potential tumor suppressor genes.

The present invention provides a non-human transgenic animal expressing a fusion construct that comprises one or more copies of cell cycle-sensitive promoter sequence operably linked to a reporter gene coding for a protein able to produce light upon metabolizing a substrate. Tumors developed within these transgenic animals will have upregulated expression of the reporter gene and, under the adequate conditions, the tumor will emit light. Increased cell cycle activity is a general characteristic in tumorigenesis; therefore, the use of a cell cycle upregulated promoter to drive reporter expression is of general use, allowing monitoring not only specific cancer types but also nearly all types of cancer.

The present invention is not limited to any one species of animal, but provides for any appropriate non-human mammal species. For example, while mice is a preferred mammal species for producing transgenic animals, other non-limiting examples including guinea pigs, rabbits, pigs, sheep, etc., may also be suitably used. The choice of transgenic animal is only limited by the ability of light generated from the expected tumors to cross tissues and reach the surface where detection can occur.

A recombinant DNA molecule is said to be capable of expressing a protein if it contains nucleotide sequences with transcriptional and translational regulatory information, and such sequences are ligated to a nucleotide sequence encoding the protein. The regulatory DNA sequence(s) and the protein-encoding DNA sequence are connected to permit gene expression. The regulatory regions needed for gene expression in general include a promoter region as well as DNA sequences which, when transcribed into RNA, will signal the initiation of protein synthesis. Such regions normally include those 5'-non-coding sequences involved with initiation of transcription and translation. A promoter region is operably linked to a DNA sequence if the promoter is capable of effecting transcription of that DNA sequence.

Transgenic animals in the present invention indicate animals in which one or more cells receive a recombinant DNA molecule. Although it is highly preferred that this molecule be integrated within the animal's chromosomes, the invention also encompasses the use of extrachromosomally replicating DNA sequences, such as yeast artificial chromosomes (Jakobovits et al., 2000). To produce transgenic animals, any method known to a person having ordinary skill in the art for introducing a recombinant construct or transgene into an embryo, such as microinjection, cell gun, transfection, liposome fusion, electroporation, and the like, may be used (see, for example, Wall et al., 1997).

The most widely used and preferred method of producing transgenic animals is microinjection which involves injecting a DNA molecule into the male pronucleus of fertilized eggs (Brinster et al, 1981). The methods of introducing a recombinant construct/transgene into mammals and their germ cells were originally developed in the mouse. These methods were subsequently adopted for use with larger animals, including livestock species. Microinjection of DNA into the cytoplasm of a zygote can also be used to produce transgenic animals. Introduction of a recombinant DNA molecule at the fertilized oocyte stage ensures that the introduced gene will be present in all the cells of the transgenic animal. Because the introduced gene will also be present in the germ cells of the transgenic founder animal, all of the founder animal's offspring will carry the introduced gene in all of their cells. Introducting the gene at a later embryonic stage might result in the absence of the introduced gene in some somatic cells of the founder animal, but the offspring of such an animal that inherit the introduced gene will carry the gene in all of their germ cells and somatic cells.

Figures 2A, 2B:
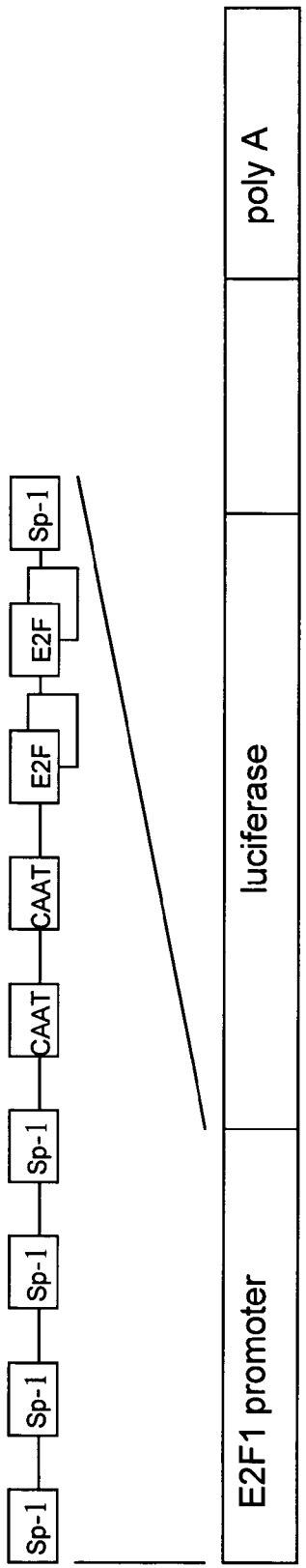
FIGS. 2A–B shows characterization of the Elux transgene.

In one embodiment of the present invention, the cell cycle-sensitive promoter region of the E2F1 gene is used to create a cell cycle reporter (FIG. 2A). The background and explanation for such a choice are discussed below. In other embodiments of the present invention, the cell cycle reporter fusions can be obtained by ligating to the reporter gene multimers or monomers of other cis-acting regulatory sequences. These regulatory sequences have to show specific up regulation upon cell cycle activity and be able to drive enough production of the reporter gene so that under the adequate conditions light emission is strong enough for visualization.

To ensure normal development and to safeguard tissue homeostasis, a set of growth-promoting and growth-inhibiting genes tightly controls cellular growth and differentiation. Alterations in the genes can lead to cellular transformation and tumor formation. There are two classes of genes whose alterations play a major role in tumorigenesis. The first class of genes is oncogenes that were initially identified in studies on retroviruses. These genes have cellular counterparts, proto-oncogenes, that promote normal cell growth; but when activated by a point mutation or induced to overexpress, these genes can promote tumorigenesis in a dominant fashion. The second class of genes is tumor suppressor genes that suppress cell growth, and their mutation or functional inactivation contribute to tumorigenesis. Unlike oncogenes, tumor suppressor genes act in a recessive manner because loss of activity requires inactivation of both alleles. Studies from a variety of human solid tumors suggest that the concerted activity of these two classes of genes underlie tumor development and progression.

Many genetic alterations involving both oncogenes and tumor suppressor genes have been associated with cancer. Both the positive and negative growth-regulatory signals act in a highly regulated manner during the G1 stage of the cell cycle by controlling the transcriptional activity of a cellular transcription factor named E2F (DeGregori, 2002) (FIG. 1). Activation of E2F is sufficient to irreversibly commit cells to undergo DNA replication, so E2F is crucial in the control of cellular proliferation in both normal and tumor cells. In fact, it seems that activation of E2F transcription factors is a key event in the malignant progression of most human malignant gliomas.

E2F acts at the level of transcriptional control of cellular genes that are essential for cell division. Among them are cell-cycle regulators (such as cyclin E, cyclin A, Cdc2, Cdc25A, the retinoblastoma protein (pRB) and E2F1), enzymes involved in nucleotide biosynthesis (such as dihydrofolate reductase, thymidylate synthetase and thymidine kinase) and the main components of the DNA-replication machinery (Cdc6, ORC1 and the mini-chromosome maintenance proteins). Regulation of the activity of one member of the E2F family, the E2F-1 transcription factor, is critical for the maintenance of normal cell proliferation control. The oncogenic ability of E2F1 has been related to its ability to up-regulate several proteins that positively regulate cell proliferation. Regulation of E2F-1 is accomplished in at least two levels: posttranslationally by binding proteins such as Rb and transcriptionally. As an example, the RNA levels of E2F1 increases about 15-fold at the G1/S-phase boundary.

In one of the embodiments of the present invention, the reporter gene used is the firefly luciferase enzyme. Luciferases are enzymes that emit light during the oxidation of its substrate luciferin. The firefly luciferase gene (luc) provides a very versatile reporter, as luciferase activity is relatively unstable in vivo. Reductions in luciferase mRNA abundance are reflected by reduced luciferase activity over several hours. The glow is widely used in in vitro cell studies as an assay for luc expression which acts as a reporter for the activity of any regulatory elements that control its expression. Luciferase is particularly useful as a reporter because low-light cameras can detect bioluminescence in real time and with high sensitivity in living cells and organisms (Langridge et al., 1994).

Other embodiments of the invention can incorporate modified versions of the luciferase enzyme, luciferase enzyme from different species or any other protein that can produce, per se, light able to cross animal tissues or any enzyme that can emit light able to cross animal tissues when provided with a suitable substrate. The genes encoding such proteins can be used as a part of the cell cycle reporter fusion construct of the present invention. Specifically the reporter protein of the present invention is limited by the fact that signal attenuation depends on the wavelength of the light being emitted and the tissue properties surrounding the emitting cells. In general, blue-green light (400–590 nm) is strongly attenuated while red to near-infrared light (590–800 nm) suffers much less attenuation. Although most types of luciferase have peak emission at blue to yellow-green wavelengths, the emission spectrum is broad enough that there is also significant emission at red wavelengths (>600 nm) that penetrate quite deeply into tissue. For small rodents such as mice, this allows detection of signals throughout the entire animal.

The limits of light detection in vivo depend on the type of bioluminescent reporter, the surrounding physiology of the animal and, most importantly, on the source depth. Subcutaneous tumors can be detected down to a few hundred tumor cells. Typically, with sensitive Charged Coupled Device (CCD) cameras, bioluminescent cells in animals can be observed from 1–3 cm deep, depending on the number and location of the cells. Scattering of photons as they propagate through tissue limits the spatial resolution of images detected on the animal surface. Roughly, spot size or resolution on the surface is approximately equal to the depth of the source below the surface. Using physics based diffusion models, improvements in spatial resolution approaching the millimeter level can be achieved. For cooled scientific grade CCD arrays the ultimate limit in signal detection is set by the read noise associated with reading CCD pixels after an image is taken, which is on the order of a few photons per pixel (Honigman et al., 2001). In some cases, there can be additional background light coming from the animal due to phosphorescence of the fur, skin, or perhaps contaminants on the animal. Typically, this background light is at a low level and only has a deleterious effect on images of deep low-level bioluminescent sources. In many cases this type of background light can be eliminated through use of an appropriate optical filter.

Bioluminescence imaging (Bhaumik and Gambhir, 2002; Hardy et al., 2001) allows rapid and noninvasive measurements of tumor development. Consecutive images from the same animal permit temporal and spatial information throughout an entire experiment instead of only at the end point. Resolution is less than with MRI or PET, but bioluminescence is better suited for high-throughput imaging because it is simple to operate, images are quick to obtain (less than one minute), several animals can be analyzed at the same time and there is no harm to the animal from the substrate luciferin since it is not toxic and it does not induce an immune reaction. Because animals recover well from gas anesthesia they can be repeatedly subject to it. Moreover, luciferase gene is co-propagated with the target cells. Therefore, external signals are proportional to tumor-cell burden (over several logs) and do not decrease as the cell population increases.

The transgenic animal of the present invention is no more susceptible to cancer than its non-transgenic counterparts. Therefore, it can be used to assess the carcinogenic potential of compounds or external insults. Moreover, specific cancer models can be generated by applying known carcinogenic compounds, viruses or processes to the transgenic animals of the present invention. The cell cycle reporter transgenic animal can be cross-bred with other animal models of cancer. By crossbreeding and inbreeding the transgenic non-human animals of the present invention, the offspring may be heterozygous or homozygous for the transgene or can be bi-transgenic (carrying two different transgenes). In this embodiment, cancer prone animals can be generated that possess an intrinsic ability, under the adequate conditions mentioned, to generate light in actively growing areas of their bodies. In this context, several types of animal cancer models have been reported that are susceptible to such a cross. They include transgenic animals that over-express one or more oncogenes, either tissue restricted or not. Another cancer model includes Knock-Out animals where one or more tumor suppressor genes have been inactivated by homologous recombination. Yet another type of animal cancer model has been generated by rendering all cells, or specific subgroups, of the animal model susceptible to infection by the high titer subgroup A avian leukosis viruses (ALV-A) through generation of transgenic animals expressing, either tissue restricted or not, the avian cell surface receptor for ALV-A (TVA). ALV-A is modified to contain exogenous genes that, when expressed, render the cells prone to neoplasia.

The cancer animal models carrying the cell cycle reporter gene generated as mentioned above can be used to: (1) assess the tumorigenic potential of oncogenes and mutated tumor suppressor genes; (2) determine the cooperative effect among oncogenes and between oncogenes and tumor suppressor genes in tumorigenesis; (3) study the sequence of tumor development including the identification of pre-neoplastic lesion, tumor invasion and metastases; (4) serve as a bioassay system for testing potential carcinogens and (5) serve as a bioassay system for testing potential anti-carcinogens.

The transgenic animals according to the present invention provide in vivo models for testing preventative measures for cancer as well as for testing novel therapeutic modalities including chemotherapy, radiation therapy, immunotherapy and gene therapy. In addition, the transgenic animals (and cells derived therefrom) of the present invention can also be used to identify antineoplastic therapeutics such as antitumor agents, which act to decrease the proliferation of cells or the growth, dissemination, or metastasis of tumors, and chemo-preventative agents, which act to inhibit the formation of new tumors. While all or some of the uses mentioned above could be derived from animal cancer models that do not possess the ability to report cell cycle activity through light emission, the added ability of bioluminescence greatly facilitates such uses of the cancer models. Far fewer animal subjects are required to obtain statistically meaningful results and because the data obtained reveal functional information, animal studies can be refined. Moreover, because the studies can be performed in minimal disease states, the stress on the animals that are studied can be reduced dramatically.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Generation of Elux Transgenic Mice

The Elux reporter transgene was constructed by ligation of the E2F1 promoter obtained from David Johnson (MD Anderson Cancer Center) with the firefly luciferase as illustrated in FIG. 2. The E2F1 promoter used includes 208 nucleotides upstream, and 66 bases downstream of the transcription site. The sequence contains several binding sites for E2F1 as well as binding sites for the transcription factor SP1. This was digested with EcoR1 and Stu1 and ligated to the gene encoding firefly luciferase digested with compatible restriction enzymes. These fragments were incubated with DNA ligase and used to transform *E. coli*. The plasmid DNA was then purified and characterized by sequence analysis. This analysis indicated a point mutation in the E2F1 promoter that resulted in a change in the sequence relative to the published sequence as indicated in FIG. 2. The mutation indicated did not affect the binding sites for any known transcription factors, and therefore was not expected to affect the activity of this construct. The construct was then tested and verified for its ability to promote expression of luciferase in cycling cells.

EXAMPLE 2

The Use of Elux Transgenic Mouse as a Glioma Animal Model

The following examples demonstrate Elux transgenic mouse can be used to monitor the formation of tumors in genetically defined tumor models such as germline modification or somatic cell gene transfer technologies.

Germline modification models of tumor formation such as transgenic mice or mice with targeted deletions, conditional knockouts, and inducible systems can be crossed into the Elux transgenic background. When these models form tumors, the deregulation of the Rb pathway is identified as the expression of the Elux transgene and detectable by bioluminescence. This allows non-invasive monitoring of tumor presence and activity in response to therapeutic and genetic intervention.

As an illustration of the use of Elux in somatic cell gene transfer models, the inventors have generated gliomas in mice harboring the Elux transgene. The Elux transgenic line was crossed with the Ntv-a transgenic mouse line. These doubly transgenic mice were then infected at birth with RCAS-PDGF. The mice were injected intracranially with one microliter containing $10^4$ DF-1 cells, a chicken fibroblast cell line that are infected with and producing the RCAS-PDGF virus. This vector encodes the PDGF B coding region downstream of the env gene and expressed from the LTR on a message that splices out the viral genes. The injection passed through the striatum, just anterior to the ventricle, until the tip of the needle just touches the skull base. The producer cells survived for only a few days within the parenchyma of the mouse brain and during this time they produced virus and infected adjacent cells expressing the receptor for RCAS, tv-a. The mice were then observed for the development of signs of intracranial pathology including weight loss, lethargy, and macrocephaly. These mice were analyzed for expression of luciferase by i.v. injection with luciferin and imaging for bioluminescence with a CCD camera as discussed in detail below.

EXAMPLE 3

In Vivo Imaging of Tumors

Animals were weighed prior to the acquisition session for proper dosage calculations. A fresh sterile solution of D-Luciferin (Xenogen, XR-1001) was prepared in the following dosage: 150 mg/kg D-Luciferin in 3 ml/kg Normal Saline. The solution was sterilized by filtration through 0.22 μm syringe filter. Individual dosages were drawn into sterile insulin syringes for each animal based on the body weight. Prior to the injection, individual syringes were kept in dark. During all the procedures D-Luciferin was protected from light.

Inhalation anesthesia machine was connected to the gas inlet hose of the IVIS. Gas inlet selector was turned into the "gas on" position. The outlet hose has to be connected to the central vacuum system and the valve open for a low flow active aspiration of the chamber air to eliminate exposure of the operator to the inhalation gas mixture and to avoid the animals' overexposure to the anesthetic. The inhalation anesthesia machine should be checked for the amounts of oxygen and Isoflurane sufficient for the whole study. The underlying black paper in the chamber was replaced for a new one prior to each animal placement. Nasal cones of the inhalation manifold were cleaned with 70% alcohol prior to each animal exposure. IVIS system should be initialized according to the product manual and the stage was moved to the preset position B for mice or D for rats. The temperature of the heated stage should be checked to be 37° C.

Oxygen flow was turned on and set for 1 l/min flow. Induction chamber and acquisition chamber vents should be open and Isoflurane dosing selector should be placed in position 4. For the induction of anesthesia, the animal was placed into the induction chamber and general activity and respiration rate were monitored. The respiration should not be slower than 1/sec. The depth of anesthesia is controlled by reaction to the noxious stimulus. Intravenous bolus injection of D-Luciferin was performed using the prepared syringe with the calculated dose. Retroorbital sinus vein is used in female mice and young animals less than 15 g in weight. The dorsal penile vein is used in males. Alternatively, tail veins may be used in both genders, but require slower rate of injection (50 μl/min). A single dose volume limit is 120 μl. Animal was placed into the acquisition chamber. The nose should be fit tightly into the inhalation manifold cone. The same procedure was repeated with the second animal. Isoflurane evaporator selector was turned to position 2 for maintaining anesthesia throughout the study. Unused outlets of the inhalation anesthesia manifolds were plugged with a rubber plug to reduce the leak of anesthetic gas mixture into the chamber.

Bioluminescent acquisition was performed according to the IVIS™ Imaging System (Xenogen). The time of acquisition of bioluminescence may vary from 5 seconds to 20 minutes. It was selected empirically, based on prior in vitro characterization of luminescence of transfected cells and the intensity of luminescence signal obtained from the current study. The acquisition time for the series of experiments within one study was fixed to allow for comparison of the results. The position of the animals in the chamber was controlled at the beginning of acquisition on the plain picture taken prior to bioluminescent acquisition. The door of the chamber had to be locked for the whole duration of acquisition. Therefore, there were no other ways to monitor the animal status throughout the experiment. For better assessment of bioluminescent signal distribution over the whole body, each animal was imaged twice in prone and supine (or right side/left side) positions during each imaging session. The total duration of imaging session, including two acquisitions (prone/supine or left/right) did not exceed 40 minutes, because d-luciferin undergoes fast biological and chemical degradation in the organism (10 minutes biohalf-life). The degradation in the luciferase expressing tissues may be higher and depends on the level of luciferase expression.

After the imaging session, the mice were removed from the chamber and monitored until complete gain of consciousness, assessed as returning to normal pattern of activity, including ambulation within the cage, grooming, eating/drinking. For the duration of the recovery period the animals were kept on bedding chips-free, warmed surface. If the recovery period lasts longer than an hour, the animal is evaluated for neurological symptoms and euthanasia is considered. After removal of the animals, the black laying paper should be replaced and the chamber should be carefully and thoroughly cleaned using Clidox solution, wiped dry to avoid chlorine induced corrosion of the equipment and ventilated to prevent intoxication of the animals imaged later with the chlorine vapors in a confined IVIS chamber.

EXAMPLE 4

Elux Transgene Activity in Mice with Brain Tumors

Figure 3A:
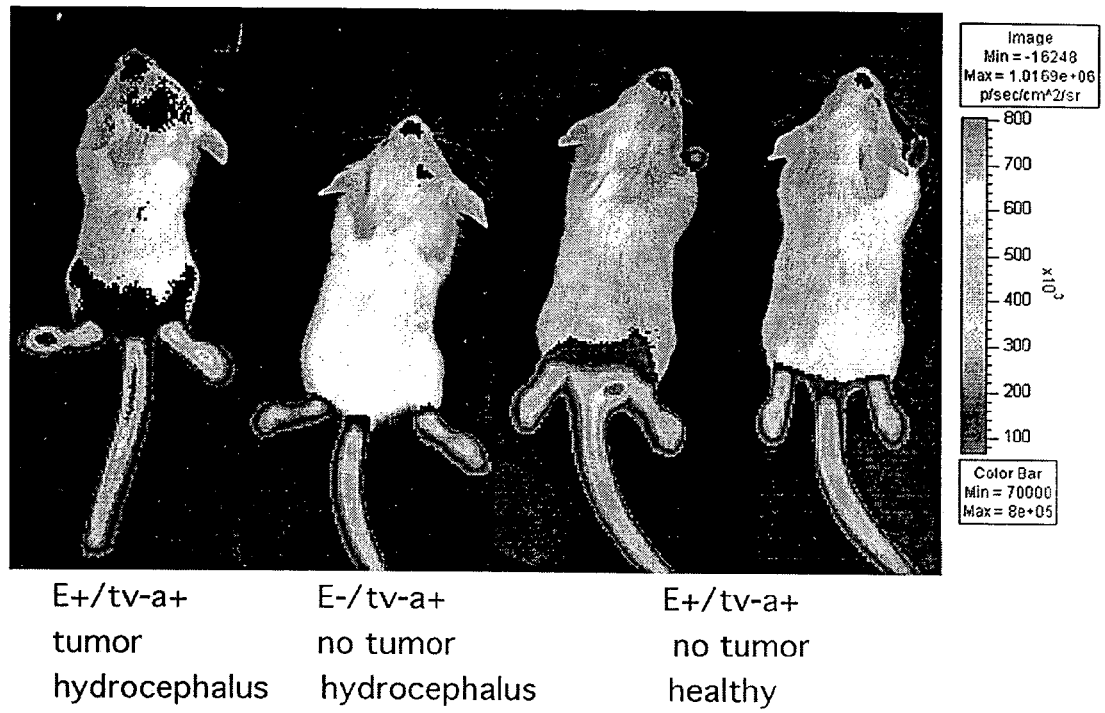
FIGS. 3A–B illustrate the activity of the Elux transgene in mice with brain tumors.
Figure 3B:
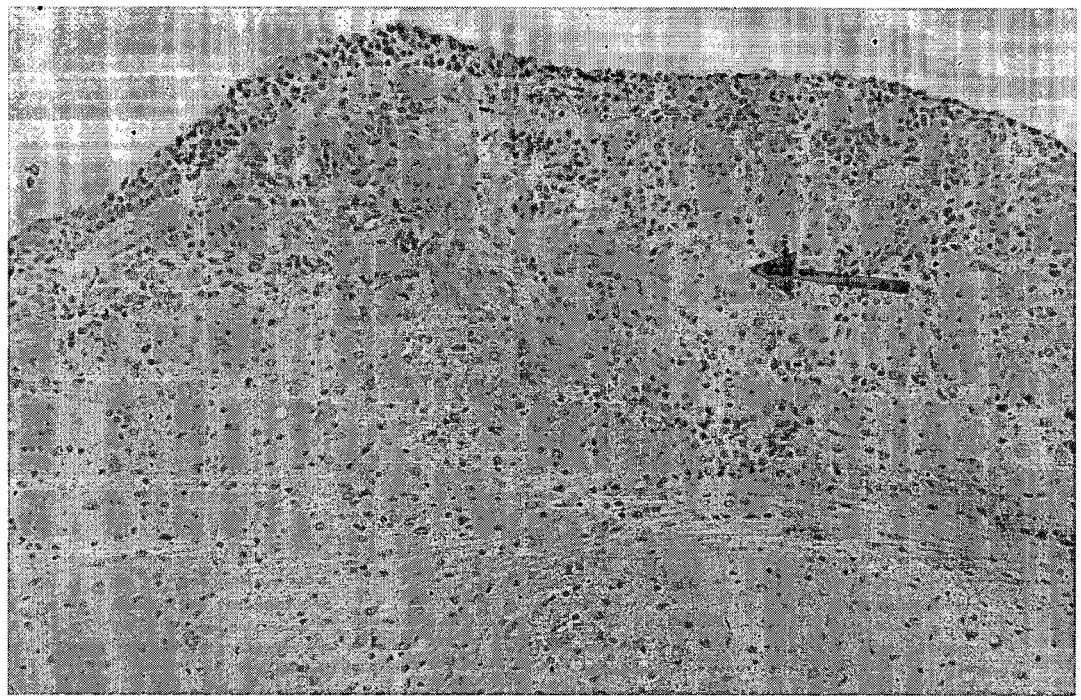

The activity of the Elux transgene in mice with brain tumors is shown in FIG. 3A. The activity in the limbs, nose and tail were due to heat radiating from the portions of the mouse not covered in fur. The brain tumors were generated by post-natal gene transfer of PDGF to CNS progenitors using the RCAS/tv-a system by virtue of the Ntv-a transgene as explained above. The histology of these tumors was that of high-grade oligodendrogliomas. The first mouse had a brain tumor and was transgenic for Elux. The signal from the brain tumor can be easily seen. The second mouse had a large brain tumor but is $Elux^{-/-}$. The slight signal was likely due to increased heat from the tumor due to elevated metabolism. The third and fourth mice were $Elux^{+/+}$ but did not have brain tumors. These data demonstrate that the presence of tumors can be detected in vivo with this system and that the activity of the Rb pathway in the tumors can be measured non-invasively allowing each mouse to act as its own control for studies on anti-neoplastic treatments. From the $Elux^+$ mice tissue was collected for histologic analysis of the glioma. FIG. 3B demonstrates intracranial luciferase activity relative to normal brain.

By using this method, real-time functional data indicating spatial distributions of tumor cells could be acquired at multiple times during the disease course. Therefore, single animal could be followed over time, removing intersample variability and improving statistical analyses. Because the extent and timing of the disease can be monitored in intact living animals, this approach allows study of early tumor growth kinetics and response to therapy with the ability to follow disease progression for weeks. It also allows for rapid optimization of therapies directed toward the control of disease at times of minimal tumor burden. Furthermore, patterns of relapse and metastases can be followed, which may help to direct the choices of treatment modalities, combination therapies, and routes of administration.

EXAMPLE 5

Response of Elux Reporter Construct to Rb Activity

Response of the reporter construct to the activity of the Rb pathway was examined as follows. First, the activity of Rb is known to respond to cell proliferation, and cells at confluence have greatly reduced E2F1 activity than do cells in log growth phase. Therefore, cells at confluence were compared with those in log growth for the luciferase expression as determined by bioluminescence. The second method for validating the response of the Elux transgene to the activity of Rb was to use a fragment of the SV40 large T antigen (T121) that blocks the function of Rb. Elux transgenic cells expressing tv-a were infected with a RCAS vector expressing T121 and then the bioluminescence was determined. Several founder lines were tested and all founder lines gave rise to cells that showed some response to Rb activity.

Cell cultures were derived from various Elux transgenic mouse lines using standard protocols known in the art. Cell cultures of primary brain cells derived from various Elux transgenic mouse lines were analyzed for transgene activity. Cells were either serum starved or allowed to grow unsynchronized in culture containing 12% of fetal calf serum and the luciferase activity was monitored. The increase in luciferase activity of these lines indicate the induction of the E2F1 driven promoter as a function of cell cycling (Table 1). In addition, the cells were transfected with an expression vector for T121, a fragment of polyoma virus large T antigen, that blocks Rb function and thereby activates the E2F1 promoter.

TABLE 1

Fold increase over non proliferating cultured cells
ELUX luc assays (cells from ELUX/J12 F1)

| Line | 12% serum (vs. 0%) | T121 infection (RCAS-T121) |
| --- | --- | --- |
| 16 | 5 | |
| 16 | 10 | |
| 16 | 11 | |
| 16 | 4 | 13 |
| 22 | 31 | |
| 22 | 51 | |
| 22 | 2 | 36 |

EXAMPLE 6

Monitoring Tumor Growth Over Time

Figure 4:
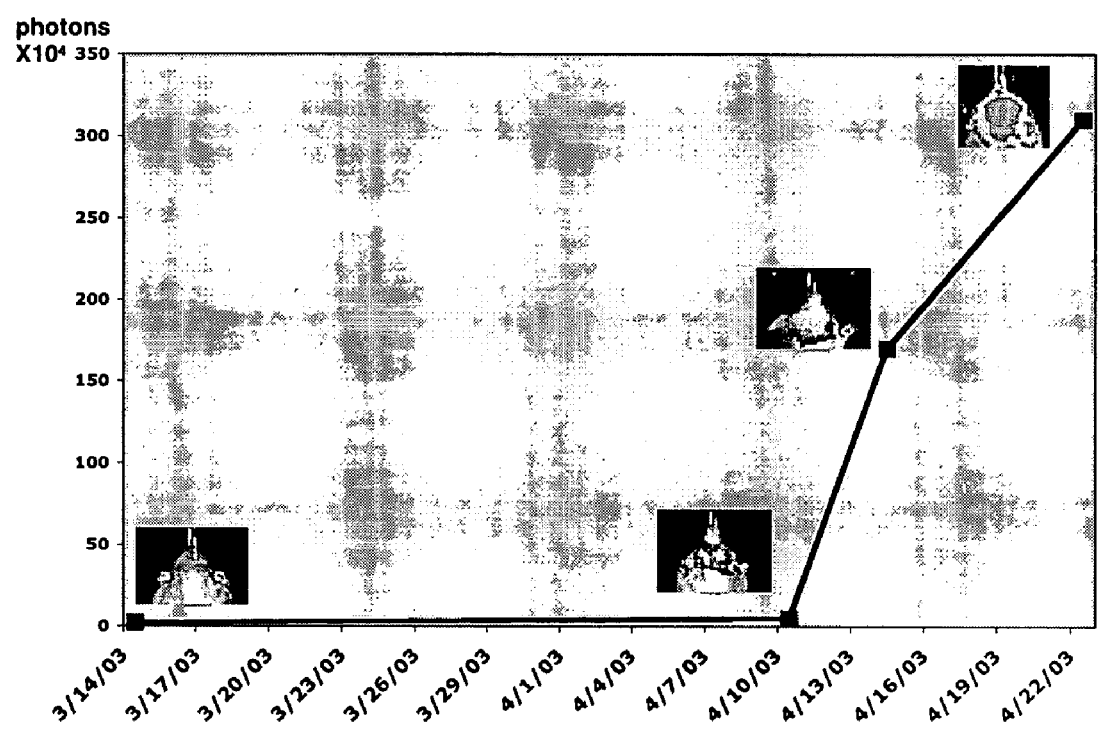
FIG. 4 shows monitoring of the growth of tumors over time. Mice were routinely and serially screened for luciferase activity. Mice will frequently develop tumors over time and initial images may not show significant amounts of bioluminescence. These mice can then be imaged frequently once the presence of tumors have been established. A time course of the development of these tumors can be completed. This time dependent increase of light production represents a summation of the tumors proliferative capacity on a per cell basis and the overall size of the tumor. The adjacent figure plots the progressive increase in bioluminescence in a mouse starting at its initial image at six weeks of age.

Mice can be routinely and serially screened for luciferase activity. Mice will frequently develop the formation of tumors over time and initial images may not show significant amounts of bioluminescence. These mice can then be imaged frequently once the presence of tumors have been established (FIG. 4). A time course of the development of these tumors can be completed. This time dependent increase of light production represents a summation of the tumors proliferative capacity on a per cell basis and the overall size of the tumor.

EXAMPLE 7

Identification of Small Tumor Lesions

Figure 5A:
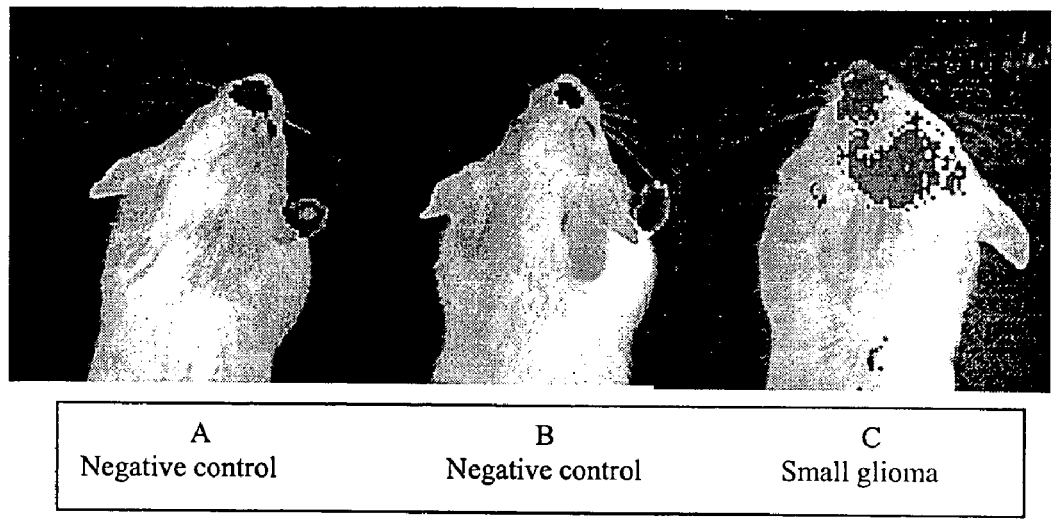
FIGS. 5A–B shows the identification of small lesions. A lesion near the detection limit was identified (FIG. 5A) and the mouse sacrificed. The entire brain was analyzed and only the minimal glioma shown here was found (indicated by the red arrow in FIG. 5B).
Figure 5B:
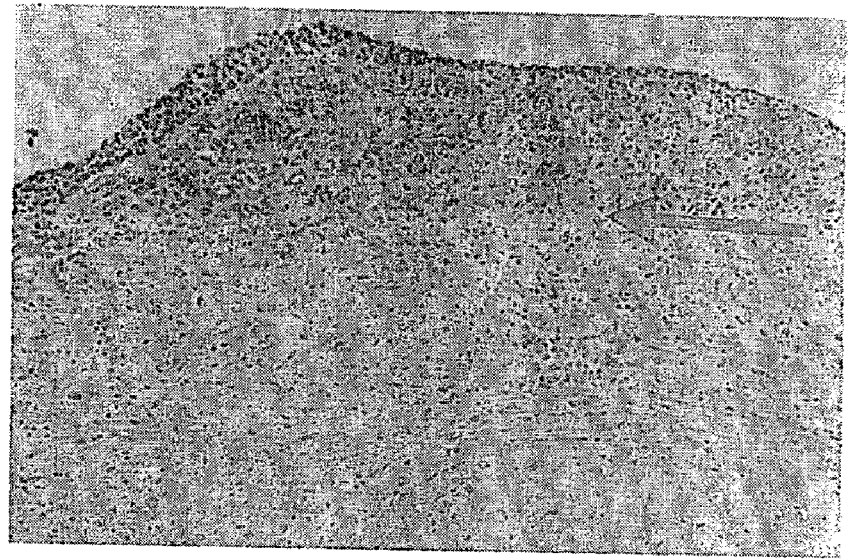

The sensitivity and flexibility of the Xenogen imaging system allows for adjustments to detect very small tumors. The exact limit on size for detection of gliomas is not known. However, in FIG. 5A it is shown the identification of a lesion near the detection limit. The mouse was sacrificed and the entire brain was analyzed. Only the minimal glioma shown in FIG. 5B was found (indicated by the red arrow). This lesion is almost certainly not detectable by MRI imaging techniques. Therefore, the Elux system is capable of detecting lesions smaller that conventional imaging techniques such as MRI.

EXAMPLE 8

Use of Elux Mice in Monitoring Therapeutic Efficacy

Figure 6:
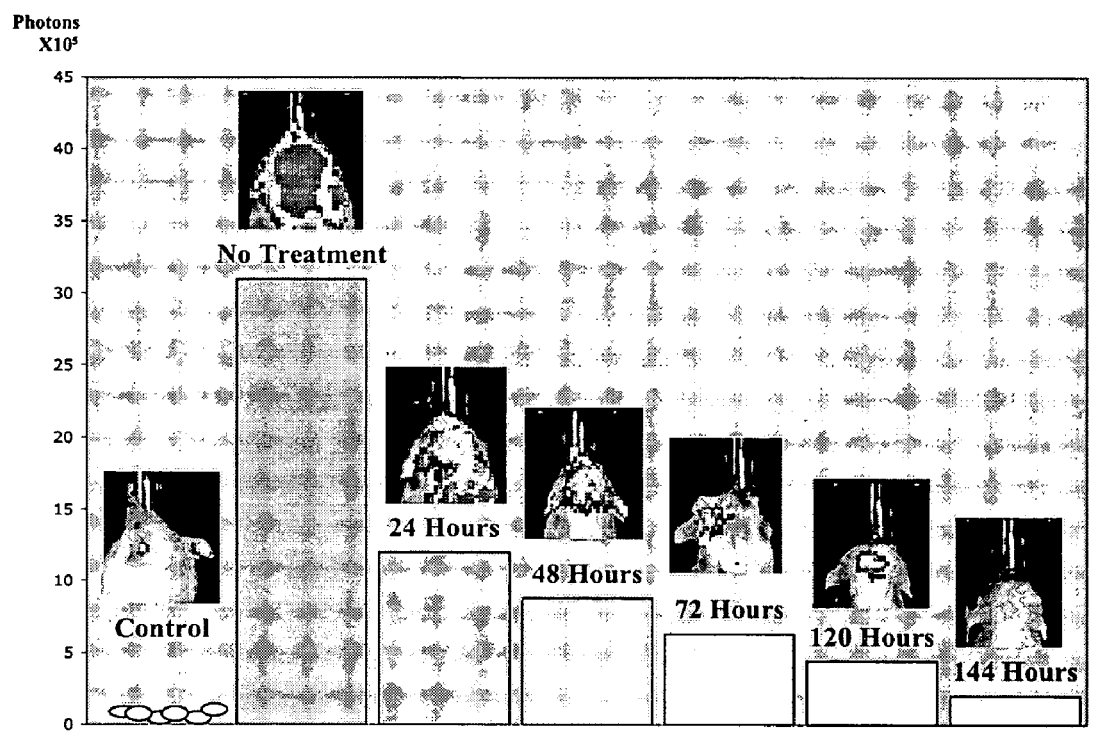
FIG. 6 shows the use of Elux mice in monitoring therapeutic efficacy. Mice bitransgenic for Ntv-a and Elux were infected with RCAS-PDGF. These mice were screened for the formation of tumors by Elux bioluminescence screening. Mice identified as having gliomas were then treated with 25 mg/kg PTK787 (Novartis) (inhibitor of PDGF receptor kinase) via i.p. injection daily. Imaging with bioluminescence daily demonstrated a substantial fall in light emission with a 50% loss in 24–36 hours.

The light production is proportional to the activity of Rb. This is either a direct or indirect effect of many of the pathways that drive cancer. Furthermore, this pathway is disrupted in most high grade cancers. Therefore, Elux activity can be a readout of the activity of this pathway as a surrogate for therapeutic effect of anticancer drugs. In this context, PDGF-driven gliomas were used and treated with PTK787, an inhibitor of PDGF receptor kinase, as proof of principle. This combination was chosen because PDGF signaling generated high Elux signaling from the gliomas in the Elux transgenic mice, and it had been demonstrated that PTK787 was capable of reversing the effects of PDGF signaling in glial cell culture. Mice bitransgenic for Ntv-a and Elux were infected with RCAS-PDGF as described above. These mice were screened for the formation of tumors by Elux bioluminescence screening. Mice identified as having gliomas were then treated with 25 mg/kg PTK787 via i.p. injection daily. Imaging with bioluminescence daily demonstrated a substantial fall in light emission with a 50% loss in 24–36 hours (FIG. 6).

Figure 7A:
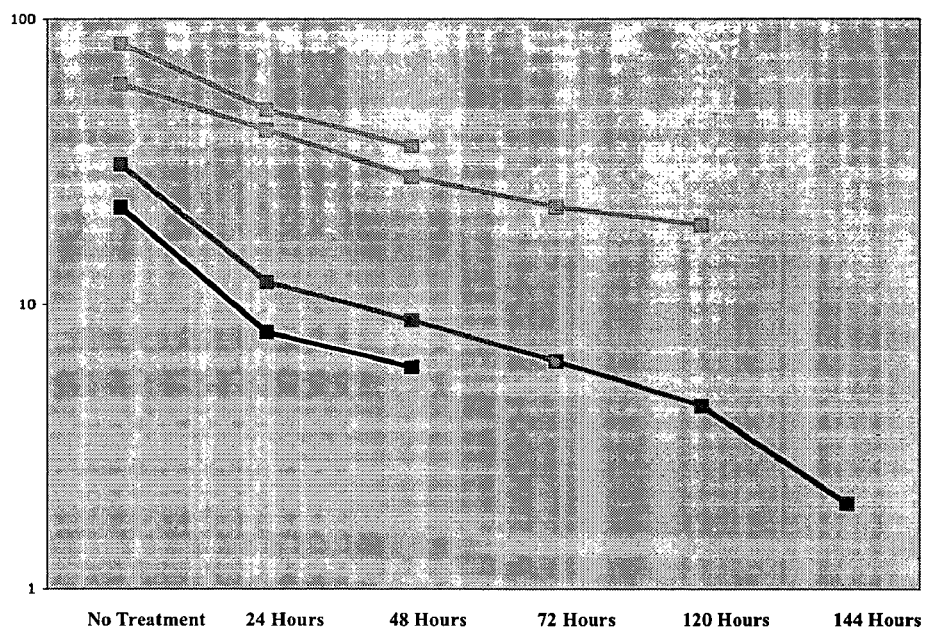
FIG. 7 shows that a readout of therapeutic effect is not dependent on the size of the tumor being treated. Several mice with PDGF-induced gliomas having various light outputs were treated with PTK787. Bioluminescence output was quantified daily during treatment. The log and the percent graph show essentially parallel responses of decreases in light emission over time with treatment.
Figure 7B:
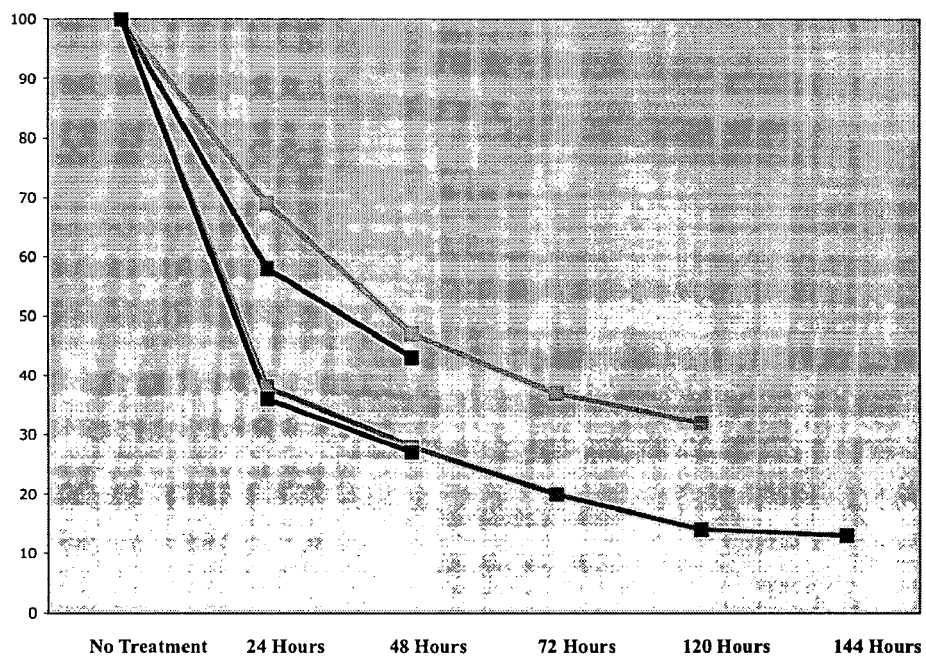

In order for the Elux mouse to be useful in preclinical therapeutic trials it would need to be reproducible. Furthermore, a readout of therapeutic effect should not be dependent on the size of the tumor being treated because many of these tumors vary in size. Therefore, the inventors treated several mice with PDGF-induced gliomas having various light outputs with PTK787. Bioluminescence output was quantified daily during treatment. It was found that for four consecutive mice the relative falloff of light production was proportionally similar. This is illustrated by the log graph showing essentially parallel responses, or the percent graph showing similar percent decreases in light over time with treatment (FIG. 7).

The following references were cited herein:

Bhaumik and Gambhir, Optical imaging of Renilla luciferase reporter gene expression in living mice. Proc. Natl. Acad. Sci. USA 99:377–382 (2002).

Brinster et al., Somatic expression of herpes thymidine kinase in mice following injection of a fusion gene into eggs. Cell 27:223–31 (1981).

DeGregori, The genetics of the E2F family of transcription factors: shared functions and unique roles. Biochim. Biophys. Acta. 1602:131–50 (2002).

Hardy et al., Bioluminescence imaging of lymphocyte trafficking in vivo. Exp. Hematol. 29:1353–60 (2001).

Honigman et al., Imaging transgene expression in live animals. Mol. Ther. 4:239–49 (2001).

Jakobovits et al., Production of transgenic mice with yeast artificial chromosomes. Methods Mol. Biol. 136:435–53 (2000).

Langridge et al., Low-light image analysis of transgenic organisms using bacterial luciferase as a marker. J Biolumin. Chemilumin. 9:185–200 (1994).

Wall et al., Transgenic animal technology. J. Androl. 18:236–9 (1997).

What is claimed is:

1. A transgenic mouse whose genome comprises a reporter gene encoding a luciferase protein, wherein said reporter gene is operably linked to an E2F1 promoter, wherein expression of said reporter gene results in detection of luciferase activity.

2. The transgenic mouse of claim 1, wherein said luciferase protein is a firefly luciferase protein.

* * * * *

SEQUENCE LISTING

<160> NUMBER OF SEQ ID NOS: 1

<210> SEQ ID NO 1
<211> LENGTH: 282
<212> TYPE: DNA
<213> ORGANISM: Artificial Sequence
<220> FEATURE:
<221> NAME/KEY: promoter
<223> OTHER INFORMATION: E2F1 promoter sequence with EcoRI sites

<400> SEQUENCE: 1

```
gaattccatc cggacaaagc ctgcgcgcgc cccgccccgc cattggccgt         50
accgccccgc gccgccgccc catcccgccc ctcgccgccg ggtccggcgc        100
gttaaagcca ataggaaccg ccgccgttgt tcccgtcacg gccggggcag        150
ccaattgtgg cggcgctcgg cggctcgtgg ctctttcgcg gcaaaaagga        200 tttgcgcgt aaaatggccg ggactttgca ggcagcggcg gccgggggcg         250
gagcgggatc gagccctcgc cgaggcctga at                           282
```